US00PP11867P2

(12) United States Plant Patent
VandenBerg

(10) Patent No.: US PP11,867 P2
(45) Date of Patent: May 8, 2001

(54) CHRYSANTHEMUM PLANT NAMED 'YOBILLINGS'

(75) Inventor: Cornelis P. VandenBerg, Salinas, CA (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 09/270,789

(22) Filed: Mar. 17, 1999

(51) Int. Cl.[7] ..... A01H 5/00
(52) U.S. Cl. ..... Plt./294
(58) Field of Search ..... Plt./294

*Primary Examiner*—Howard J. Locker
(74) *Attorney, Agent, or Firm*—C. A. Whealy

(57) ABSTRACT

A distinct cultivar of Chrysanthemum plant named 'Yobillings', characterized by its mostly upright and uniformly mounded plant habit; freely branching habit, very full and dense plants; uniform and early flowering; vigorous and strong plant growth; numerous and very large daisy inflorescences that are about 13.2 cm in diameter when grown as a disbud; white-colored ray florets; slow maturing green-colored disc florets; and good postproduction longevity with inflorescences and leaves maintaining good substance and color for about three weeks in an interior environment.

2 Drawing Sheets

BACKGROUND OF THE INVENTION

The present invention relates to a new and distinct cultivar of Chrysanthemum plant, botanically known as *Dendranthema grandiflora* and hereinafter referred to by the cultivar name Yobillings.

The new Chrysanthemum is a product of a planted breeding program conducted by the Inventor in Salinas, Calif. The objective of the breeding program is to create new pot-type Chrysanthemum cultivars having desirable inflorescence forms and floret colors and good post-production longevity.

The new Chrysanthemum originated from a cross made by the Inventor in January, 1991, in Salinas, Calif., of a proprietary Chrysanthemum seedling selection identified as code number YB-4684 as the male, or pollen, parent, with a proprietary Chrysanthemum seedling selection identified as code number YB-5163 as the female, or seed, parent.

The new Chrysanthemum was discovered and selected by the Inventor as a flowering plant within the progeny of the stated cross in a controlled environment in Salinas, Calif., in November, 1992. The selection of this plant was based on its desirable inflorescence form and floret colors and good post-production longevity.

Asexual reproduction of the new Chrysanthemum by terminal cuttings harvested in a controlled environment in Salinas, Calif., has shown that the unique features of this new Chrysanthemum are stable and reproduced true to type in successive generations.

SUMMARY OF THE INVENTION

The cultivar Yobillings has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yobillings'. These characteristics in combination distinguish 'Yobillings' as a new and distinct Chrysanthemum:

1. Mostly upright and uniformly mounded plant habit.

2. Freely branching habit, very full and dense plants.

3. Uniform and early flowering.

4. Vigorous and strong plant growth.

5. Numerous and very large daisy inflorescences that are about 13.2 cm in diameter when grown as a disbud.

6. White-colored ray florets.

7. Slow maturing green-colored disc florets.

8. Good postproduction longevity with inflorescenes and leaves maintaining good substance and color for about three weeks in an interior environment.

The new Chrysanthemum can be compared to the Chrysanthemum cultivar White Blush, disclosed in U.S. Plant Pat. No. 9,441. However in side-by-side comparisons in Salinas, Calif., and Leamington, Ontario, Canada, under commercial practice, plants of the new Chrysanthemum differ from plants of the cultivar White Blush in the following characteristics:

1. Plants of the new Chrysanthemum are taller, much more vigorous and stronger than plants of the cultivar White Blush.

2. Leaves of the new Chrysanthemum are less likely to fleck than leaves of the cultivar White Blush.

3. Inflorescences of the new Chrysanthemum are slightly larger, fuller and have more ray florets than inflorescences of the cultivar White Blush.

4. Ray florets of the new Chrysanthemum are more white in color, more upright, appear fresher and have better substance than ray florets of the cultivar White Blush.

5. Disc florets of the new Chrysanthemum are slower to mature and maintain their green color longer than disc florets of the cultivar White Blush.

BRIEF DESCRIPTION OF THE PHOTOGRAPHS

The accompanying colored photographs illustrate the overall appearance of the new Chrysanthemum showing the colors as true as it is reasonably possible to obtain in colored reproductions of this type.

The photograph at the top of the first sheet comprises a side perspective view of a typical flowering plant of 'Yobillings'.

The photograph at the bottom of the first sheet comprises a close-up view of a typical inflorescence and upper (left) and lower (right) surfaces of typical leaves of the cultivar Yobillings.

The photograph at the top of the second sheet comprises a side perspective view of typical flowering plants of 'Yobillings' (left) and 'White Blush' (right).

The photograph at the bottom of the second sheet comprises a close-up view of upper surfaces of typical inflorescences of plants of 'Yobillings' (left) and 'White Blush' (right). Floret and foliage colors in the photographs may appear different from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown in Salinas, Calif., and Leamington, Ontario, Canada, under greenhouse conditions which approximate those generally used in commercial potted Chrysanthemum production. Four unrooted cuttings were directly stuck in a 15-cm container and pinched once. Plants used for this description were grown as disbud-types. Measurements and numerical values represent averages of typical flowering plants.

Botanical classification: *Dendranthema grandiflora* cultivar Yobillings.

Commerical classification: Decorative disbud or spray-type pot Chrysanthemum.

Parentage:

*Male or pollen parent.*—Proprietary *Dendranthema grandiflora* seedling selection identified as code number YB-4684.

*Female or seed parent.*—Proprietary *Dendranthema grandiflora* seedling selection identified as code number YB-5163.

Propagation:

*Type.*—Terminal tip cuttings.

*Time to rooting.*—Seven to ten days with soil temperatures of 21° C.

*Rooting habit.*—Fine, fibrous and well-balanced.

Plant description:

*Appearance.*—Herbaceous daisy pot Chrysanthemum that can be grown as a disbud or spray. Inverted triangle; stems mostly upright and somewhat spreading giving a uniformly mounded appearance to the plant. Freely branching; about four or five lateral branches develop after removal of terminal apex (pinching); dense and full plants.

*Plant height.*—Tall, about 35 cm.

*Plant width.*—About 44 cm.

*Stem color.*—Close to 147A.

*Stem texture.*—Pubescent.

*Foliage description.*—Arrangement: Alternate. Length: About 9.3 cm. Width: About 6.8 cm. Apex: Mostly acute. Base: Attenuate. Margin: Palmately lobed, sinuses between lateral lobes mostly parallel to slightly convergent. Texture: Upper and lower surfaces with very fine pubescence; veins prominent on lower surface. Petiole length: About 2.9 cm. Color: Young foliage upper surface: 147A. Young foliage lower surface: Slightly darker than 147B. Mature foliage upper surface: 147A. Mature foliage lower surface: Close to 147B. Venation upper surface: Close to 147B. Venation lower surface: 147B.

Inflorescence description:

*Appearance.*—Very large daisy inflorescence form with elongated ray florets. Inflorescences borne on terminals above foliage, arising from leaf axils. Disk and ray florets arranged acropetally on a capitulum.

*Flowering response.*—Under natural conditions, plant flowers in the autumn/winter in the Northern Hemisphere. At other times of the year, inflorescence initiation and development can be induced under short day/long night conditions (at least 13.5 hours of darkness). Plants exposed to two weeks of long day/short night conditions after planting followed by photoinductive short day/long night conditions flower about eight weeks later.

*Postproduction longevity.*—Inflorescences and leaves will maintain good color and substance for about three weeks in an interior environment.

*Quantity of inflorescences.*—As a disbud-type, all lateral inflorescences are removed to allow for maximum terminal inflorescence size. One inflorescence per lateral stem; about five inflorescences per plant.

*Inflorescence bud.*—Height: About 6.5 mm. Diameter: About 8.5 mm. Color: Close to 141A.

*Inflorescence size.*—Diameter: About 13.2 cm. Depth (height): About 2.8 cm. Diameter of disc: About 2.5 cm.

*Ray florets.*—Shape: Elongated with short corolla tube. Orientation: Mostly flat; angled somewhat upright. Length: About 6.4 cm. Width: About 1.45 cm. Apex: Typically acute. Margin: Entire. Texture: Smooth, glabrous, satiny. Number of ray florets per inflorescence: About 42. Color: When opening: Slightly ivory to white, 155D. Fully opened, upper surface: White, 155D. Fully opened, lower surface: White, 155D.

*Disc florets.*—Shape: Tubular. Apex: Serrated, flared. Length: About 8 mm. Width: Apex: About 2.5 mm. Base: About 1.5 mm. Number of disc florets per inflorescence: More than 200. Color: Immature: Greener than 154A; slower maturing, green color maintained. Mature: Apex: 9A. Mid-section: Light green. Base: White.

*Reproductive organs.*—Androecium: Present on disc florets only. Anther color: 13A. Pollen: Amount: Scarce. Color: 14A. Gynoecium: Present on both ray and disc florets.

Disease resistance: Resistance to pathogens common to Chrysanthemums has not been observed on plants grown under commercial greenhouse conditions.

Seed production: Seed production has not been observed.

It is claimed:

1. A new and distinct cultivar of Chrysanthemum plant named 'Yobillings', as illustrated and described.

* * * * *

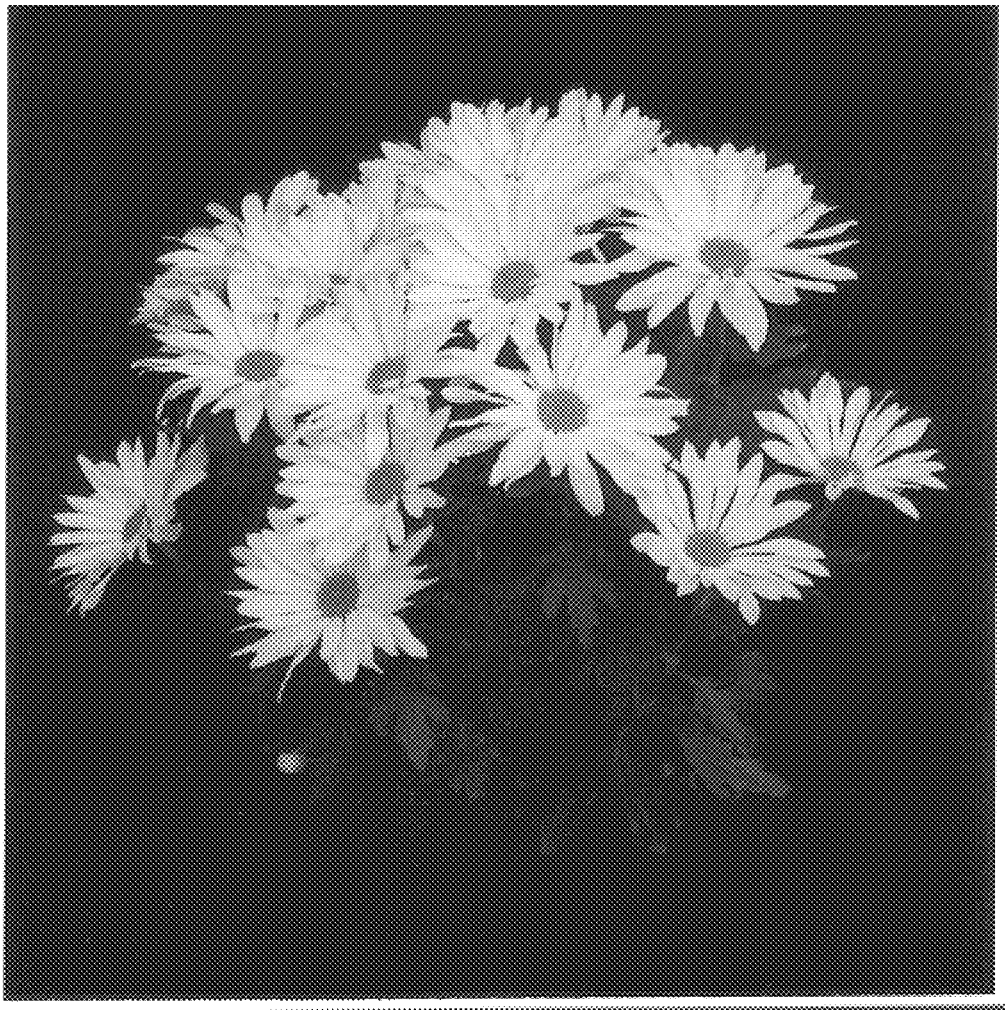
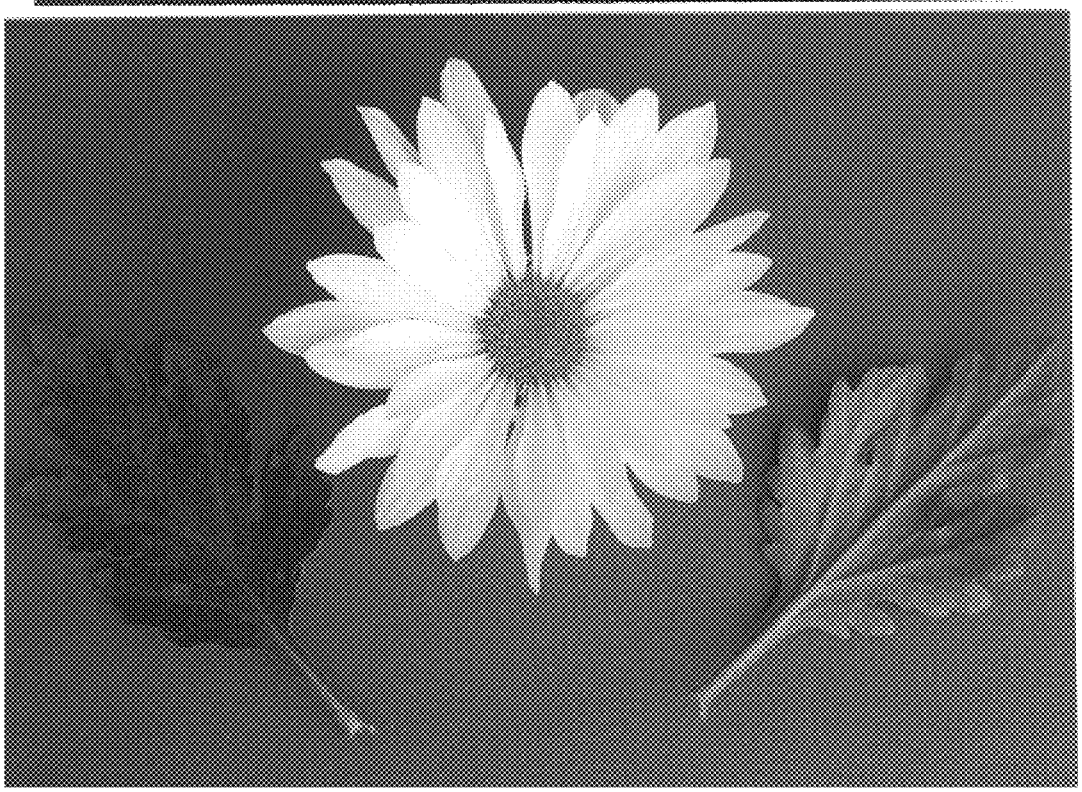

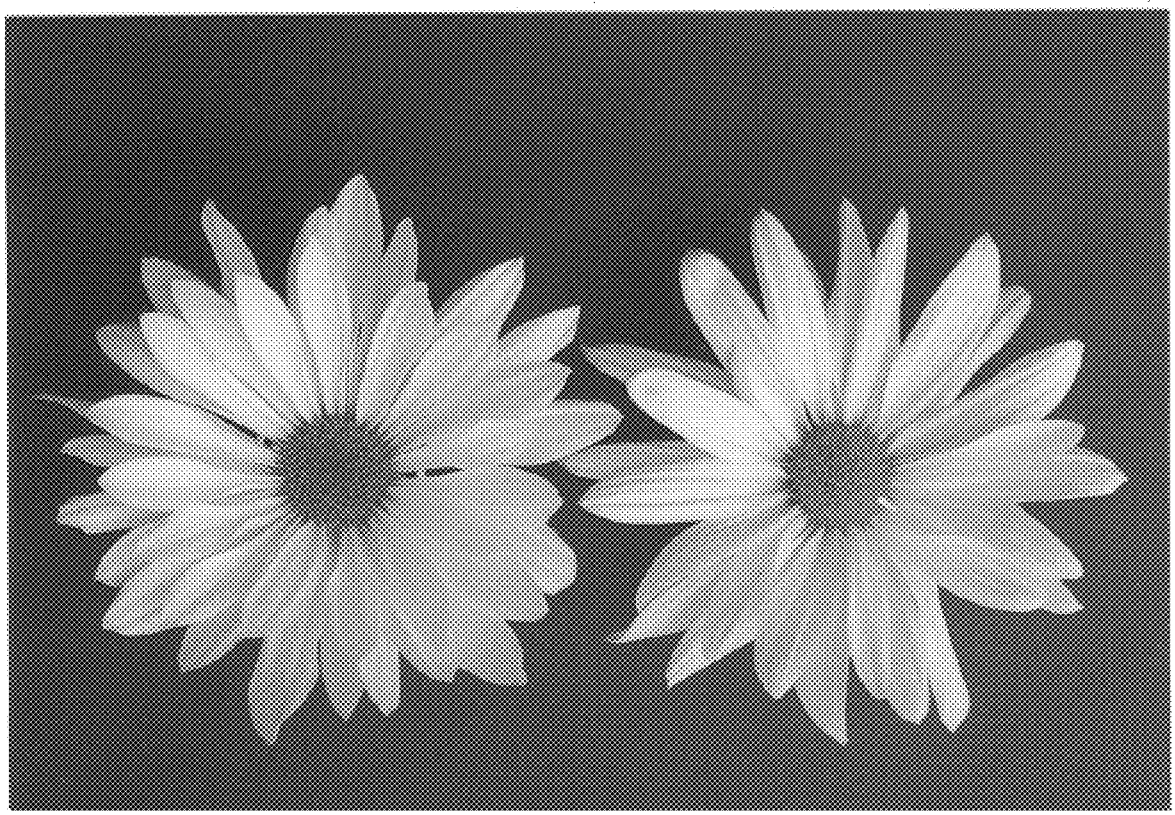

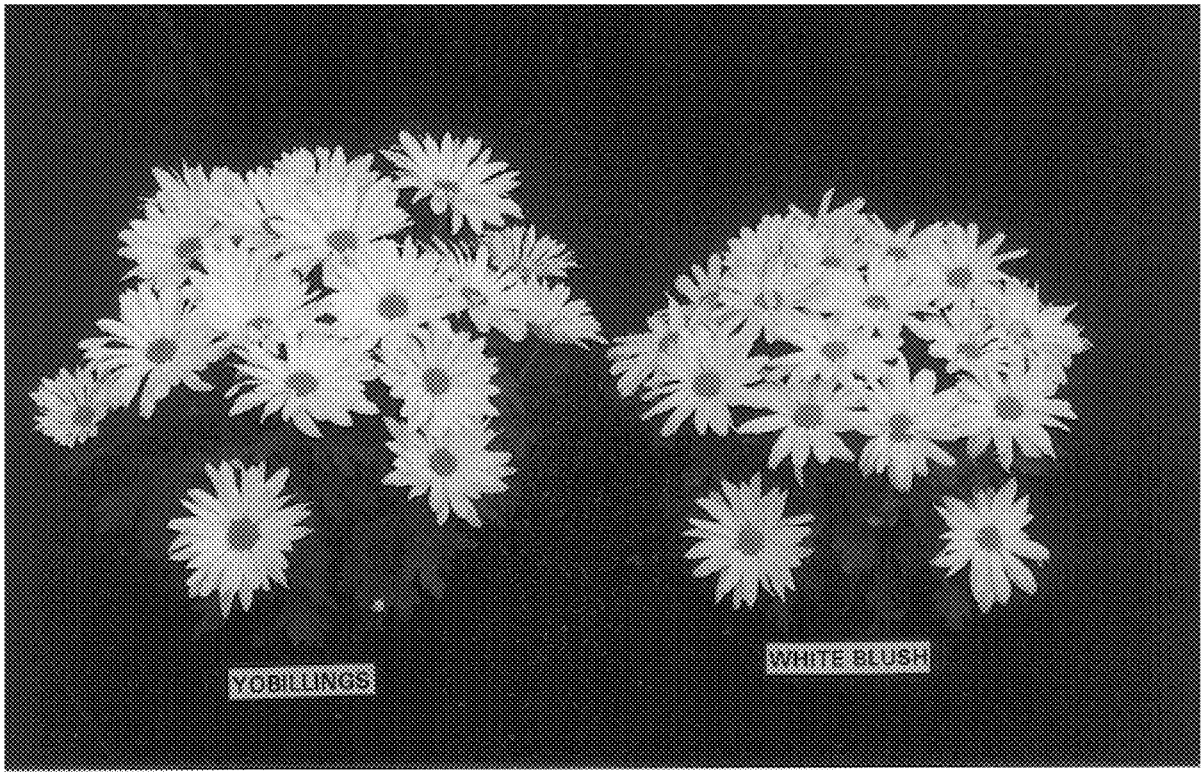
YOBILLINGS
WHITE BLUSH